United States Patent [19]

Grous et al.

[11] Patent Number: 5,185,362
[45] Date of Patent: Feb. 9, 1993

[54] DIPHENYLAMINE CARDIOVASCULAR AGENTS, COMPOSITIONS AND USE

[75] Inventors: Philip P. Grous, Philadelphia; Richard J. Mohrbacher, Maple Glen, both of Pa.

[73] Assignee: McNeilab, Inc., Spring House, Pa.

[21] Appl. No.: 728,791

[22] Filed: Jul. 8, 1991

Related U.S. Application Data

[63] Continuation of Ser. No. 532,137, May 31, 1990, abandoned, which is a continuation of Ser. No. 244,772, Sep. 14, 1988, abandoned.

[51] Int. Cl.$^5$ .............. A61K 31/40; C07D 295/088
[52] U.S. Cl. ................... 514/428; 548/569
[58] Field of Search .................. 548/569; 514/428

[56] References Cited

U.S. PATENT DOCUMENTS

| | | | |
|---|---|---|---|
| R. 30,577 | 4/1981 | Busch et al. | 544/124 X |
| 4,430,338 | 2/1984 | Jansen et al. | 514/428 |
| 4,555,514 | 11/1985 | Combourieu et al. | 514/343 |
| 4,645,778 | 2/1987 | Monteil et al. | 514/422 |
| 4,727,072 | 2/1988 | Grous et al. | 514/230 |
| 4,758,563 | 7/1988 | Grous et al. | 514/233.8 |
| 4,762,834 | 8/1988 | Combourieu et al. | 514/252 |

FOREIGN PATENT DOCUMENTS

| | | |
|---|---|---|
| 37537 | 8/1952 | Australia . |
| 0138684 | 4/1985 | European Pat. Off. . |
| 0146155 | 6/1985 | European Pat. Off. . |
| 0146159 | 6/1985 | European Pat. Off. . |
| 2558159 | 7/1985 | France . |
| 83/02274 | 7/1983 | PCT Int'l Appl. . |

*Primary Examiner*—Joseph Paul Brust

[57] ABSTRACT

Propylamines of the formula (I):

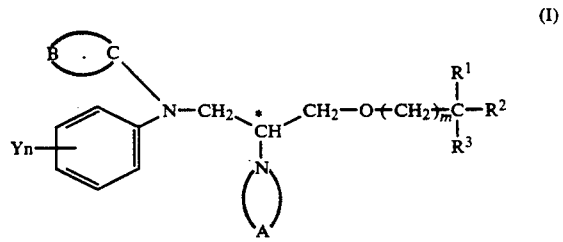

and isomers thereof, particularly those enantiomers and racemates relative to the chiral carbon indicated by an asterisk (*). The propylamines can be used for the treatment of hypertension or angina in humans. A is pyrrolidine, piperidine or morpholine and B is an aromatic heterocycle, aromatic carbocycle or saturated carbocycle.

10 Claims, No Drawings

DIPHENYLAMINE CARDIOVASCULAR AGENTS, COMPOSITIONS AND USE

This is a continuation of application Ser. No. 07/532,137, filed May 31, 1990, which is a continuation of application Ser. No. 07/244,772, filed Sep. 14, 1988, both now abandoned.

Various ethers are known to be effective cardiovascular pharmaceuticals as described in U.S. Pat. No. 4,555,514; U.S. Pat. No. 30,577; PCT Publication 83/-2274; Australian patent 85/37537; French Brevet 2,558,159; and European Patent Applications 138,684; 146,155 and 146,159. Our U.S. Pat. Nos. 4,727,072 and 4,758,563 and copending U.S. Ser. No. 190,550, filed May 5, 1988, now abandoned, also describe such compounds.

SUMMARY OF THE INVENTION

Propylamines of the following formula (I):

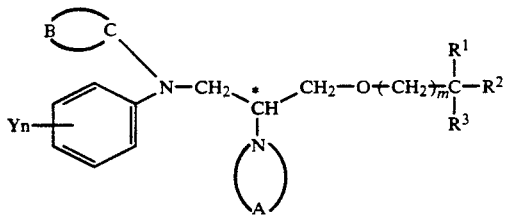

(I)

are provided as antihypertensive and anti-anginal agents which can be used in a manner similar to bepridil. In formula (I), $R^1$—$R^3$ are alkyl or joined to form cycloalkyl, A is pyrrolidine, piperidine or morpholine, Y is as described, n is 0–3 and B is an aromatic or saturated ring with or without substitution.

DETAILED DESCRIPTION OF THE INVENTION

In more detail, the invention includes propylamines of the following formula (I):

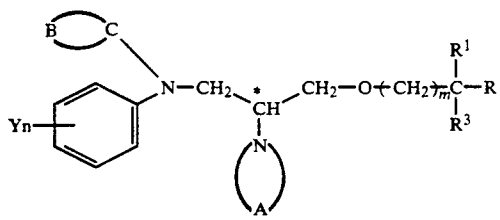

(I)

wherein
$R^1$, $R^2$ and $R^3$ are lower alkyl groups or $R^1$ is a lower alkyl group and $R^2$ and $R^3$ are joined to form a cycloalkyl group of about 3 to 7 carbons or $R^1$, $R^2$ and $R^3$ are joined to form a polycyclicalkyl group of about 7 to 12 carbons;
m is 0 or 1;
A represents the atoms necessary to form a pyrrolidine, piperidine or morpholine ring;
Y is independently selected from the group consisting of halo, alkyl, alkoxy, trifluoromethyl, hydroxy, or, when n is 2 on adjacent carbons, methylenedioxy;
n is 0, 1, 2 or 3; and
B represents the atoms necessary to form an aromatic heterocyclic ring, a saturated carbocyclic ring or an aromatic carbocyclic ring wherein said aromatic carbocyclic ring is either unsubstituted or is independently substituted by 1 or 2 of halo, alkyl, alkoxy, trifluoromethyl, hydroxy, monoalkylamino, dialkylamino or methylenedioxy;
and the pharmaceutically acceptable acid addition salts thereof.

Within the scope of $R^1$, $R^2$ and $R^3$ are lower alkyl groups of about 1 to 6 carbons such as methyl, ethyl, n-propyl and iso-propyl, the individual $R^1$, $R^2$ and $R^3$ groups being independently chosen, with methyl being particularly preferred. Thus, a particular alkoxymethyl group of the invention is that where $R^1$, $R^2$ and $R^3$ are all methyl. A second arrangement for $R^1$—$R^3$ is that where $R^1$ is an alkyl as described and $R^2$ and $R^3$ together represents a saturated hydrocarbon cyclic moiety of about 3 to 10 carbons, e.g. a cyclopentyl or cyclohexyl ring. A third arrangement for $R^1$—$R^3$ is where all three are part of a saturated hydrocarbon cyclic moiety, e.g. 1-adamantyl, 1-bicyclo[2.2.2]octane or 1-bicyclo[2.2.1-]heptane.

m is, in particular, 1.

A represents particularly the atoms necessary to form a pyrrolidine ring.

Y is halo such as fluoro, chloro, bromo, or iodo; alkyl of about 1 to 6 carbons such as methyl, ethyl, n-propyl or tert-butyl; alkoxy of about 1 to 6 carbons such as methoxy, ethoxy or sec-butoxy; $CF_3$; OH; or when n is 2 at adjacent carbons, Y can be methylenedioxy.

n is 0–3, particularly 2 such as the 2 and 6 positions although all such positional isomers are contemplated, e.g. 2,3; 3,5; etc. Particular Y substitution includes 2,6-dichloro, 3-methoxy, 2-chloro, 2,6-dimethyl, 3-trifluoromethyl, 2,6-dibromo and 2-chloro-6-methyl.

B includes aromatic heterocyclic rings of 5 or 6 members, e.g. those having a single N, S or O as the heteroatom such as 2- or 3-pyrrolyl, 2- or 3-thienyl or 2- or 3-furanyl or 2-, 3- or 4-pyridinyl, or two heteroatoms such as pyrazinyl. Also within the scope of B are saturated carbocyclic rings of about 3 to 10 carbons such as cyclopropyl, cyclopentyl and cyclohexyl rings. The last group of B rings are the aromatic carbocyclic rings such as phenyl which may be unsubstituted or substituted independently by 1 or 2 of halo, such as fluoro, chloro, bromo or iodo; alkyl of about 1 to 6 carbons such as methyl or ethyl; alkoxy of about 1 to 6 carbons such as methoxy, ethoxy or tert-butoxy; $CF_3$; OH; monoalkylamino of about 1 to 6 carbons such as methylamino or sec-butylamino dialkylamino of about 2 to 12 carbons such as dimethylamino or N-sec-butyl-N-methylamino; or methylenedioxy at adjacent carbons. Particular examples of B ring groups are phenyl, 4-dimethylaminophenyl, 3,4-dimethoxyphenyl, 4-pyridinyl and cyclohexyl.

Particular examples of compounds of the invention of formula (I) are:
N-(2,6-dichlorophenyl)-beta-[[(1-methylcyclohexyl)-methoxy]-methyl]-N-phenyl-1-pyrrolidineethanamine; and
N-(2,6-dimethylphenyl)-beta-[[(1-methylcyclohexyl)-methoxy]-methyl]-N-phenyl-1-pyrrolidineethanamine.

Representative salts of the compounds of formula (I) which may be used include those made with acids such as hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluene sulfonic, cyclohexanesulfamic, salicylic, p-aminosalicylic, 2-phenoxybenzoic, 2-acetoxybenzoic or a salt made with saccharin. Such salts can be made by reacting the free base of (I) with the acid and recovering the salt.

Compounds of Formula (I) and other compounds of the invention may exist in various isomeric forms, e.g., in view of the presence of an asymmetric carbon. Examples include the asymmetric carbon directly attached to the nitrogen of the pyrrolidine. It is understood that the present invention includes all such individual isomers and their racemates. Particular isomers are the R and S isomers relative to symmetry at the carbon in formula (I) below marked by an asterisk (*). Such individual isomers may be obtained as known in the art, e.g. by initiating the synthesis with optically active starting materials or reagents or by separation of racemic intermediates or final products, e.g. as described in "Stereochemistry of Carbon Compounds", by Ernest L. Eliel, McGraw-Hill, New York (1962) and "Enantiomers, Racemates and Resolutions" by Jean Jacques et al., John Wiley & Sons, New York (1981). Also within the scope of the invention are compounds of the invention in the form of hydrates and other solvate forms. "Alkyl" as used herein denotes straight and branched chain alkyl.

To prepare compounds of the present invention having formula (I), one may use the reaction sequences summarized in the following Reaction Scheme wherein R is used to refer to the —(CH$_2$)$_m$—C(R$^1$R$^2$R$^3$) moiety in formula (I) and the remaining symbols are as defined for formula (I) compounds, e.g., the A and B rings, Y, etc.

Reaction Scheme:

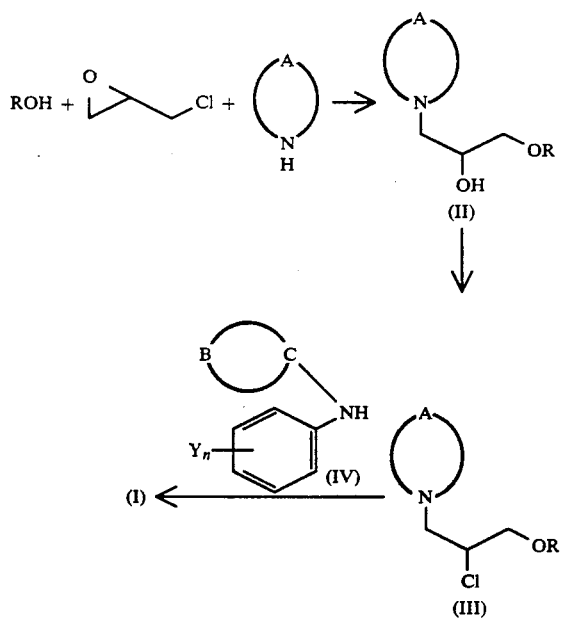

Alcohols of formula ROH may be obtained commercially, prepared as known in the art or synthesized from the corresponding acid of formula (R$^1$R$^2$R$^3$C)COOH by reduction, e.g., with borane or other reducing agents. Epichlorohydrin and the A ring heterocyclic compound are commercially available or known in the literature.

Amino alcohols of the formula (II) may be prepared by stirring 1.0 mole of the starting alcohol ROH and 1.0 mole of epichlorohydrin and adding 0.001 mole of a Lewis acid such as titanium (IV) chloride, zinc (II) chloride, boron trifluoride or tin (IV) chloride. The reaction temperature rises to about 160° C. in a few seconds and is stirred until the reaction temperature is about 40° C. followed by the addition of 1.0 mole of the A ring heterocycle. The reaction mixture is stirred and heated on a steam bath for 1 hr, allowed to return to room temperature and 25% sodium or potassium hydroxide solution containing 1 mole of hydroxide is added with stirring. The reaction mixture is heated on a steam bath for 30 min, then cooled to room temperature, partitioned between cold water and ether and the ether layer is dried, the solvent is removed and the residue distilled under reduced pressure to give the amino alcohol (II).

The intermediate (II) is then reacted with a chlorinating agent such as PCl$_5$, PCl$_3$ or SOCl$_2$ to yield the chloro compounds of formula (III). In a typical procedure, 109.4 g (0.525 m) of phosphorous pentachloride and 60 ml of dry toluene are stirred in an inert atmosphere and cooled in ice while a solution of 0.5 m of the amino alcohol (II) hydrochloride in 150 ml of dry toluene is added dropwise at a rate to keep the reaction temperature below 10° C. When the addition is complete, the ice bath is removed and stirring is continued at RT for 2 hrs. The resulting solution is added dropwise at a rate to keep the reaction temperature below 25° C. to a stirred solution of 4.5 m of potassium hydroxide in cold water while cooling in an ice bath. Stirring is continued for 30 min after the addition is complete and the reaction mixture is partitioned between toluene and water. Occasionally, an immiscible oily layer forms between the layers. In this case, the oil and the organic layers can be combined. The toluene layer or the toluene and oil layers are washed with water, dried and concentrated to dryness in vacuo at less than 50° C. The crude product is stored under argon in the refrigerator until used.

The chloro compound of formula (III) may then be directly reacted with a secondary aniline of formula (IV) to yield (I). Reaction of the chloro compound (III) to yield (I) involves a transition state moiety formed by loss of Cl— and migration of the N-A ring to the carbon which formerly carried the chlorine.

In more detail, the reaction of (III) with the secondary aniline (IV) may be carried out by dropwise addition of a solution of 1.1 eq of (III) and 1.0 eq of secondary aniline (IV) in dry toluene at about 100° C. to a stirred mixture of 1 or more eq of sodium hydride and about 0.01 to 0.1 eq of potassium hydride in dry toluene under argon or nitrogen. The reaction mixture is stirred, heated to reflux for about 4 to 80 hrs, cooled to RT and partitioned between water and toluene and/or ether. The organic portion is purified by chromatography, distillation and/or crystallization. In an alternative procedure, a solution of 1.0 or more eq of methyl lithium in ether is added dropwise to a stirred solution of 1.0 eq of the secondary aniline (IV) in dry THF under argon or dry nitrogen. The reaction mixture is stirred for 1 or more hrs, a solution of 1.0 eq of (III) in dry tetrahydrofuran is added dropwise and the reaction mixture is heated to reflux for 3 to 16 hrs. The reaction mixture is cooled to RT, diluted with ether, extracted with water and the organic portion is purified by chromatography, distillation or crystallization.

Other alkyl lithium compounds that may be used in this alternative procedure are n-butyl lithium in hexane and sec-butyl lithium in cyclohexane.

The activity of compounds of formula (I) for the treatment of hypertension was determined using the Spontaneously Hypertensive Rat (SHR) test as described below.

SPONTANEOUSLY HYPERTENSIVE RAT TEST

In this test, the arterial pressure of adult spontaneously hypertensive rats (Charles Rivers) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hr. A test compound is considered to be active as an antihypertensive agent if the mean arterial pressure (MAP) indicates a fall of >15 mm of Hg. Each animal serves as its own control.

In the SHR test, the products of Examples 1e and 2b when tested by the oral route at 30 mg/kg were found to have $\Delta$ MAP values of $-53$ and $-46$ mm of Hg, respectively.

CORONARY BLOOD FLOW TEST (CBF)

In addition to their utility in the treatment of hypertension, the compounds of formula (I) are useful in the treatment of the symptoms of angina pectoris by virtue of their ability to increase coronary blood flow. The activity of compounds of formula (I) in the treatment of angina was determined using the Coronary Blood Flow Dose-Response Profile in the Anesthetized Dog (CBF) Test as described below.

Mongrel dogs are anesthetized with sodium pentobarbital and ventilated with a positive pressure respirator. Catheters are implanted into the right femoral artery and right atrium and connected to pressure transducers for the measurement of their respective pressures. The right femoral vein is cannulated for drug infusion. A thoracotomy is then performed via the left fifth intercostal space. Coronary blood flow is measured by placing an electromagnetic flow transducer around the left circumflex coronary artery and connected to a flowmeter. All the data are recorded on a strip-chart recorder. Six to seven doses of the test compounds are infused intravenously via the right femoral vein at a dose range of 0.025 to 2 mg/kg. The doses for each compound are infused sequentially with each dose infused over a five minute period. Arterial and atrial pressures, coronary blood flow, calculated vascular resistance and heart rate are monitored continuously and the data summarized at control, the end of infusion for each dose and at 15 min after the end of infusion.

In the CBF Test, the product of Example 2b caused a dose-related increase in coronary blood flow (max= +140% from control) and a fall in calculated vascular resistance (max= −67% from control). The $ED_{50}$ for the increase in flow was 0.25–0.5 mg/kg, i.v., when both arterial pressure and heart rate were not affected. Arterial pressure and heart rate decreased significant only at the dose-range of 1-2 mg/kg, i.v.

To prepare the pharmaceutical compositions of this invention, one or more compounds or salts thereof of the invention as the active ingredient, is intimately admixed with a pharmaceutical carrier according to conventional Pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 50 to about 1000 mg of the active ingredient, and, preferably, from about 100 to about 500 mg.

Also within the scope of the invention are methods for the treatment of hypertension or angina pectoris by administration of pharmaceutically effective amounts of a compound of formula (I) in admixture with a pharmaceutically acceptable diluent or carrier.

In the following examples and throughout the specification, the following abbreviations may be used: mg (milligrams); g (grams); kg (kilograms); ml (milliliters); m (moles); mmole (millimoles); M (molar); N (normal); psi (pounds per square inch); mp (melting point); bp (boiling point); meq (milliequivalents); eq (equivalents); E (trans); Z (cis); $BH_3$ (borane); $B_2H_6$ (diborane); $Et_2O$ (diethyl ether); EtOAc (ethyl acetate); MeOH (methanol); EtOH (ethanol); LAH (lithium aluminum hydride); THF (tetrahydrofuran); DMF (dimethylformamide); MTBE (methyl tert-butyl ether); IPA (isopropyl alcohol); hr (hours); min (minutes); RT (room temperature); p.o. (per os, orally); i.p. (intraperitoneal); and C,H,N,O, etc. (the chemical symbols for the elements) Unless otherwise indicated, all temperatures are reported in °C. (degrees centigrade) and all references to ether are to diethyl ether.

EXAMPLE 1 a. 1-Methyl-1-cyclohexylmethanol

A three liter, three necked round bottom flask was equipped with a thermometer, magnetic stirrer, argon inlet and outlet adapters and a one liter addition funnel containing 922 ml of 1.0 molar $BH_3.THF$. 1-Methyl cyclohexanecarboxylic acid (119.2 g; 0.84 m) was added to the reaction vessel and dissolved in 100 ml of THF. The reaction mixture was cooled with an ice bath to 5° C. and the BH$_3$.THF was added dropwise over 25 min maintaining the temperature between 5°–15° C. After the addition was complete, the ice bath was removed. After about five min, the reaction exothermed and foamed violently. A much slower addition rate and constant cooling should help to avoid this exotherm. The reaction was allowed to stir for two hr at RT under nitrogen, then 150 ml of methanol was added cautiously. When the foaming ceased, the reaction was concentrated in vacuo using low heat and the residue was treated with 100 ml of 5% acetic acid. After stirring for thirty min, the reaction was transferred to a one liter separatory funnel, diluted with water (slurry dissolved) and extracted three times with ether. The combined ether extracts were washed twice with saturated sodium bicarbonate, twice with brine, dried over anhydrous magnesium sulfate, filtered through celite and concentrated in vacuo (low heat) to give 79.09 g of a clear water-white oil. The oil was distilled on a Kugelrohr apparatus at 75°–130° C. (25 mm of Hg). Most distilled at 90° C. to give 72.11 g of 1-methyl-1-cyclohexylmethanol.

b. alpha-[((1-Methylcyclohexyl)methoxy)methyl]-1-pyrrolidineethanol

A two liter three necked round bottom flask was equipped with a mechanical stirrer, condenser, thermometer, two neck adapter, drying tube, and a nitrogen inlet. 1-Methyl-1-cyclohexylmethanol (71.2 g; 0.555 m) (the compound of Example 1a.) was added to the reaction vessel followed by 100 ml of xylene and 43.4 ml (0.555 m) of epichlorohydrin. The reaction was heated to 50° C. while stirring under nitrogen. 1.45 g (0.0056 m) of SnCl$_4$ was added. The reaction exothermed suddenly to 140° C. and slowly cooled to 50° C. The reaction was kept at 50° C. in a water bath for 1.5 hr, then cooled to 5° C. with an ice bath. Cold 20% sodium hydroxide (prepared from 40 g of 50% NaOH) was added followed by 47.4 g (0.666 m) of pyrrolidine. The ice bath was removed, the reaction was heated to reflux for one hr, cooled to RT, diluted with about one liter of water and extracted twice with ether. The combined ether extracts were washed with water, brine, dried over anhydrous potassium carbonate, filtered through dicalite and concentrated in vacuo to give 143.39 g of crude product a light yellow viscous oil. The crude oil was distilled twice to yield 77.6 g (55%) of the title compound, b.p. 139°–154° C. (0.025 mm).

c. 1-[2-Chloro-3-(1-methylcyclohexyl)methoxypropyl]-pyrrolidine

A 500 ml three necked round bottom flask was equipped with a mechanical stirrer, addition funnel, thermometer and an argon inlet and outlet. PCl$_5$ (33 g; 0.159 m) and 18 ml of dry toluene was added to the reaction vessel. 38.5 g (0.151 m) of alpha-[((1-methylcyclohexyl)methoxy)methyl]-1-pyrrolidineethanol (the compound of Example 1b.) was added to the addition funnel along with 45 ml of toluene. Hydrogen chloride gas was bubbled into the addition funnel until the solution was acidic. The PCl$_5$ suspension was cooled to 10° C. and the amino alcohol hydrochloride solution was added dropwise, maintaining the temperature between 10°–15° C. After the addition was complete, the ice bath was removed and the mixture stirred at RT for 1.5 hr. A two liter beaker containing 116 ml of 45% potassium hydroxide and 210 g of ice was cooled in an ice bath. The reaction mixture (a clear yellow solution) was transferred to a separatory funnel and added portionwise at a rate to keep the reaction temperature at 25°–35° C. Stirring was continued for 0.5 hr after the addition. The reaction was transferred to a two liter separatory funnel and diluted with water and ether. The water layer was extracted twice with ether and the combined ether extracts were washed twice with water, once with brine, dried over anhydrous potassium carbonate and concentrated in vacuo to give 29.12 g of the title compound.

d. N-phenyl-2,6-dichloroaniline

The title compound may be prepared as set forth in German Democratic Republic Patent 141,306 dated Apr. 23, 1980 as abstracted in Chemical Abstracts 94 174615k (1981) or as set forth in the J. Taiwan Pharm. Assoc. 29 120 (1977).

e. N-(2,6-dichlorophenyl)-β-[[(1-methylcyclohexyl)-methoxy]methyl]-N-phenyl-1-pyrrolidineethanamine perchlorate (1:1)

A 250 ml, 3-necked, round bottom flask was equipped with a magnetic stirrer, addition funnel, argon inlet and outlet and a silicone oil bath. Sodium hydride (60%, 2.19 g, 1.2 eq) was added to the reaction vessel and extracted twice with Et$_2$O under argon. Diglyme (50 ml) was then added followed by potassium hydride (50 mg). The slurry was heated to 110° C. under argon with stirring. To the addition funnel was then added N-phenyl-2,6-dichloroaniline (11.21 g, 0.0456 m) (the product of Example 1d.) and 1-[2-chloro-3-(1-methylcyclohexyl)methoxypropyl]pyrrolidine (15 g, 0.0548 m) (the product of Example 1c) which was diluted with 20 ml of diglyme. The mixture was added dropwise over 15 min, allowing for the smooth evolution of hydrogen gas. The reaction is slightly exothermic. After 15 min, the reaction mixture was cooled to RT, quenched with 20 ml of H$_2$O and concentrated on a rotary evaporator. The orange residue was partitioned between H$_2$O and CH$_2$Cl$_2$. The H$_2$O layer was extracted twice with CH$_2$Cl$_2$ and the combined CH$_2$Cl$_2$ extracts were washed with H$_2$O, brine, dried over anhydrous K$_2$CO$_3$, filtered through diacalite and concentrated under vacuum to give 24.1 g (93% yield) of the title product as an orange oil. The product was purified on a preparative, high pressure liquid chromatography apparatus using hexane; acetone (92:8) to give 19.56 g of product. The product was dissolved in 75 ml of absolute EtOH and treated with 1.0 eq (3.53 ml of 70% of HClO$_4$) and crystals were allowed to form at RT for 1 hr and in an ice bath for 2 hr. The crystals were filtered and air dried with suction to give 19.29 g of the title product. The product was recrystallized from EtOH, mp 183°–185° C.

Elemental Analysis Calculated: C, 56.31; H, 6.48; N, 4.86; Found: C, 56.39; H, 6.48; N, 4.77

EXAMPLE 2 a. N-phenyl-2,6-dimethylaniline

The product may be prepared as described by C. Izard-Verchere et al. in the Bulletin of Chemical Society of France, 2122–2134 (1971).

b.
N-(2,6-Dimethylphenyl)-β-[[(1-methylcyclohexyl)-methoxy]methyl]-N-phenyl-1-pyrrolidineethanamine hydrochloride (1:1)

In a 1 liter, 3-neck, round bottom flask under a nitrogen atmosphere were placed 100 ml of sieve dry toluene, 1.32 g of 80% NaH/oil and a small amount of KH/oil. The mixture was stirred, heated to reflux and to it was added dropwise a solution of 7.89 g of N-phenyl-2,6-dimethylaniline, the product of Example 2a, and 13.14 g of the chloramine product of Example 1c in 100 ml of sieve dry toluene over a 50 min period. The mixture was stirred and heated to reflux for 22.5 hr. The reaction mixture was then cooled to RT and to it was added an ether/water mixture. Two layers were separated from each other and the organic layer was washed one time with water and once with brine. The organic layer was evaporated to leave 20.74 g of oil which was purified by flash chromatography to yield 11.02 g of oil. The oil was dissolved in ethyl acetate to which was added Et$_2$O.HCl. The mixture was concentrated to dryness to yield a foamy oil which was dissolved in ethyl acetate. Ether and hexane were added to the cloud point, and the mixture was allowed to crystallize and the crystals collected. The product was recrystallized from CH$_2$Cl$_2$ to yield 6.51 g of a white solid, mp 197°–199° C.

Elemental Analysis Calculated: C, 73.93; H, 9.20; N, 5.95; Found: C, 73.96; H, 9.24; N, 5.90

What is claimed is:

1. A propylamine compound selected from the group consisting of:
    N-(2,6-dichlorophenyl)-beta-[[1-methylcyclohexyl)-methoxy]-methyl]-N-phenyl-1-pyrrolidineethanamine;
    N-(2,6-dimethyphenyl)-beta-[[(1-methylcyclohexyl)-methoxy]-methyl]-N-(phenyl)-1-pyrrolidineethanamine; and a pharmaceutically acceptable acid addition salt thereof.

2. The propylamine of claim 1, wherein said propylamine is N-(2,6-dichlorophenyl)-beta-[[1-methylcyclohexyl)methoxy]-methyl]-N-phenyl-1-pyrrolidineethanamine and a pharmaceutically acceptable acid addition salt thereof.

3. The propylamine of claim 1, wherein said propylamine is N-(2,6-dimethyphenyl)-beta-[[(1-methylcyclohexyl)-methoxy]-methyl]-N-(phenyl)-1-pyrrolidineethanamine; and a pharmaceutically acceptable acid addition salt thereof.

4. The propylamine of claim 2, wherein said salt is the hydrochloride salt.

5. A pharmaceutical composition for use in treating hypertension which comprises the propylamine of claim 1, in an effective amount for treating hypertension in combination with a pharmaceutically acceptable diluent or carrier.

6. A method for treating hypertension in a mammal which comprises administering to the mammal a composition of claim 1.

7. The method of claim 6, wherein the mammal is a human.

8. A pharmaceutical composition for use in treating angina, which comprises the propylamine of claim 1, in an effective amount for treating angina in association with a pharmaceutically acceptable diluent or carrier.

9. A method for the treatment of angina in a mammal which comprises administering to the mammal the compound of claim 1, in an amount effective for the treatment of angina.

10. The method of claim 9, wherein the mammal is a human.

* * * * *